United States Patent [19]

Hirsch et al.

[11] 4,171,239
[45] Oct. 16, 1979

[54] METHOD AND APPARATUS FOR APPLYING ADHESIVE ATTACHING TAPES TO PADS

[75] Inventors: John L. Hirsch; Edmund A. Radzins, both of Sheboygan Falls, Wis.

[73] Assignee: Curt G. Joa, Inc., Sheboygan Falls, Wis.

[21] Appl. No.: 400,091

[22] Filed: Sep. 24, 1973

[51] Int. Cl.$^2$ ............................................. B32B 31/00
[52] U.S. Cl. ..................................... 156/461; 156/519
[58] Field of Search ................. 156/66, 519, 521, 444, 156/289, 200, 203, 204, 226, 227, 461, 463, 465, 466, 201; 128/284, 287, 288, 290 R, 291 R; 93/82, 84; 83/154, 341; 270/41, 86, 94

[56] References Cited

U.S. PATENT DOCUMENTS

| | | | |
|---|---|---|---|
| 2,140,213 | 12/1938 | Tegarty | 156/203 |
| 2,667,909 | 2/1954 | Stobb | 156/444 |
| 3,008,364 | 11/1961 | Stobb | 83/154 X |
| 3,174,372 | 3/1965 | Huck | 83/341 X |
| 3,288,757 | 3/1976 | deNeui | 156/461 |
| 3,322,600 | 5/1967 | Harrison et al. | 156/519 X |
| 3,355,995 | 12/1967 | Borkmann et al. | 156/521 X |
| 3,642,001 | 2/1972 | Sabee | 128/287 |
| 3,673,019 | 6/1972 | Erekson | 156/66 |

*Primary Examiner*—David A. Simmons
*Attorney, Agent, or Firm*—Joseph P. House, Jr.

[57] ABSTRACT

Method and apparatus for applying adhesive attaching tapes to pads, such as diapers, in which an elongated strip of adhesive tape having an adhesive face and a non-adhesive back is folded longitudinally about a hinge line to form tape wings having their non-adhesive backs together and their adhesive faces facing away from each other. A release liner is applied to the adhesive face of one of the wings, leaving the adhesive face of the other wing exposed. Discrete folded tape segments are severed from the folded strip and are transferred from the vicinity of the severing tool to the vicinity of the pad by drawing the lined wings of the folded tape segments by vacuum against a vacuum drum. The adhesive face of the exposed wing faces outwardly of the drum. The drum is rotated to adhere the adhesive face of the exposed wing to a portion of the pad in the course of drum rotation. The lined wing is then free to have the liner stripped therefrom and unfolded about the hinge line for application of the exposed wing to another portion of the pad.

11 Claims, 13 Drawing Figures

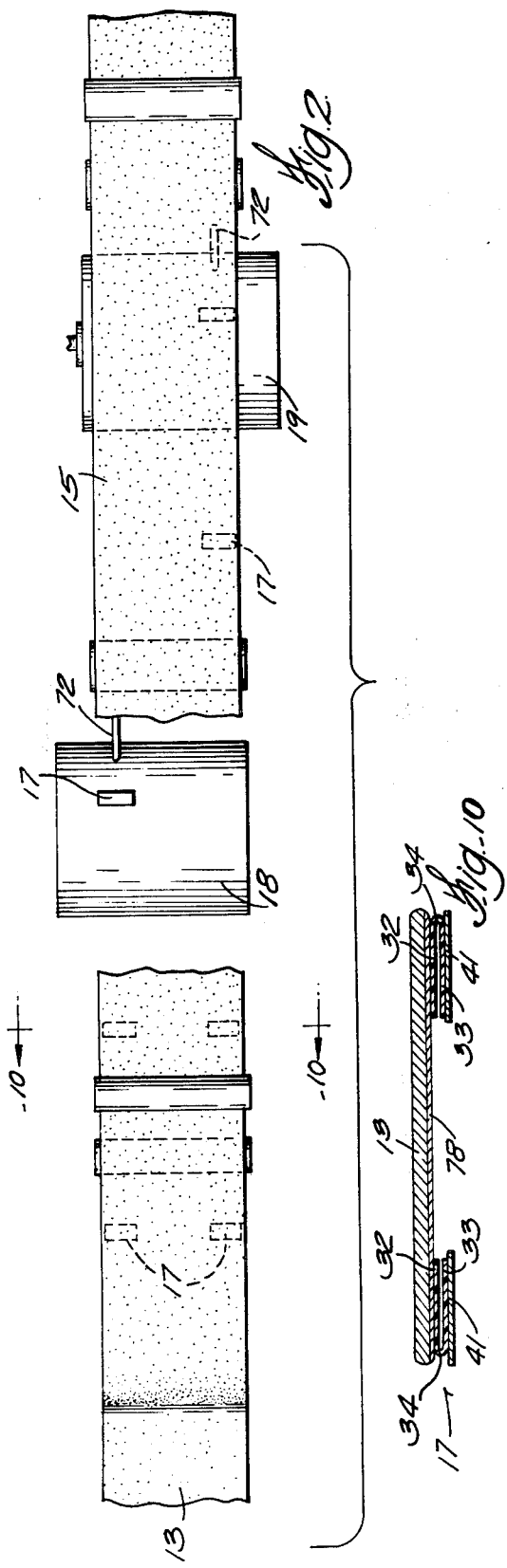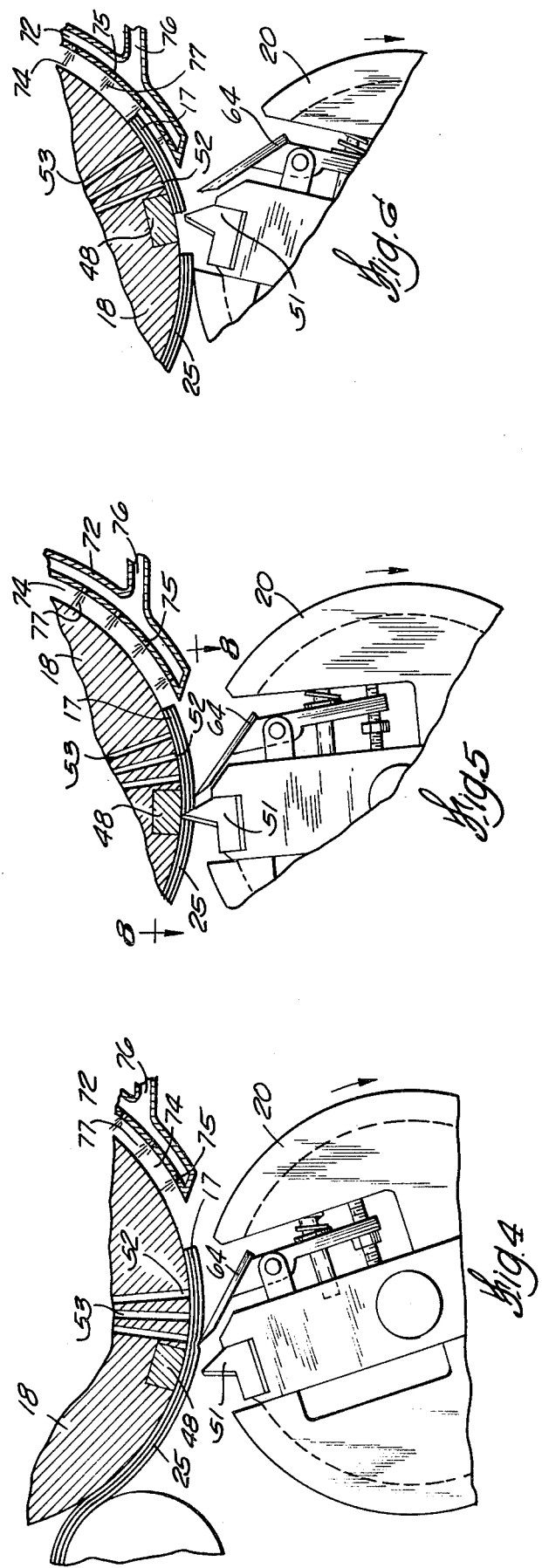

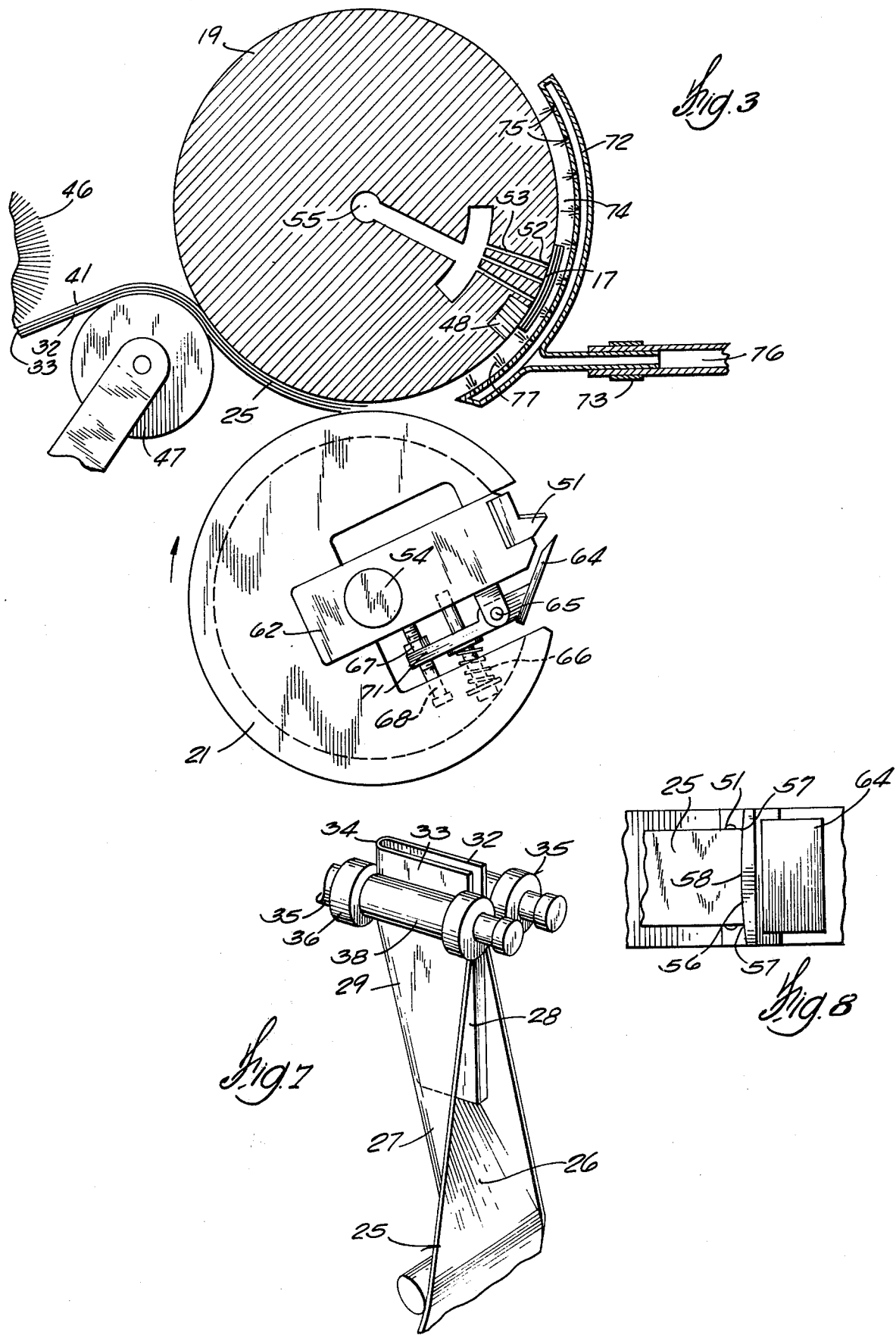

4,171,239

METHOD AND APPARATUS FOR APPLYING ADHESIVE ATTACHING TAPES TO PADS

BACKGROUND OF THE INVENTION

Present techniques for applying attaching tapes to pads such as diapers either do not locate the tapes advantageously with respect to the pad or involve production bottlenecks. Copending U.S. patent application Ser. No. 196,118 filed Nov. 5, 1971, now U.S. Pat. 3,772,120, discloses a technique utilizing a vacuum drum which efficiently applies tapes to pads, but does not locate the tape on the pad to achieve the advantages of the present invention.

SUMMARY OF THE INVENTION

In accordance with the present invention, a rotary vacuum pad is utilized to apply tape segments to diapers or like pads and by which said segments are advantageously located on the diaper pad in such a way that the adhesive side of the tape segment at both ends of the tape is adhered to the plastic backing of the diaper. The tape segment is adhered to the outside face of the diaper pad and is hence protected by the pad thickness from exposure to dampness.

In accordance with the present invention, a folded tape segment is transferred from the vicinity of a severing tool to the pad by means of a rotary vacuum drum to which the lined wing of a folded tape segment is held by vacuum with the exposed adhesive face of the other wing facing outwardly therefrom. The tendency of the exposed wing to spring away from the lined wing about its hinge line is overcome during the course of rotation of the drum for example, by the impingement of an air blast against the exposed wing as the drum is rotated. An alternative technique is to use a guide rail which mechanically prevents the exposed wing from springing away from the lined wing. Moreover, a spring-actuated blade is desirably employed to hold the wings together beyond the point at which the tape segment is severed and until the tape segment is under the influence of the tape guide.

Other objects, features and advantages of the invention will appear from the following disclosure.

DESCRIPTION OF THE DRAWINGS

FIG. 2 is a diagrammatic top view of apparatus shown in FIG. 1.

FIG. 3 is an enlarged detail view showing the relationship of the rotary knife drum and the vacuum drum.

FIGS. 4, 5 and 6 are sequential views showing successive positions of the rotary knife and vacuum drums in the course of the coaction therebetween in which the knife will sever a tape segment from the tape strip and the segment is transferred from the vicinity of the knife to the zone of influence of the air guide.

FIG. 7 is a perspective view illustrating the folding of the tape strip about a tape folder blade.

FIG. 8 is a fragmentary detailed view illustrating the manner of coaction between the curved knife and the drum anvil to shear cut the tape segment from the tape. This view is taken along the line 8—8 of FIG. 5.

FIG. 10 is a cross section along the line 10—10 of FIG. 2.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
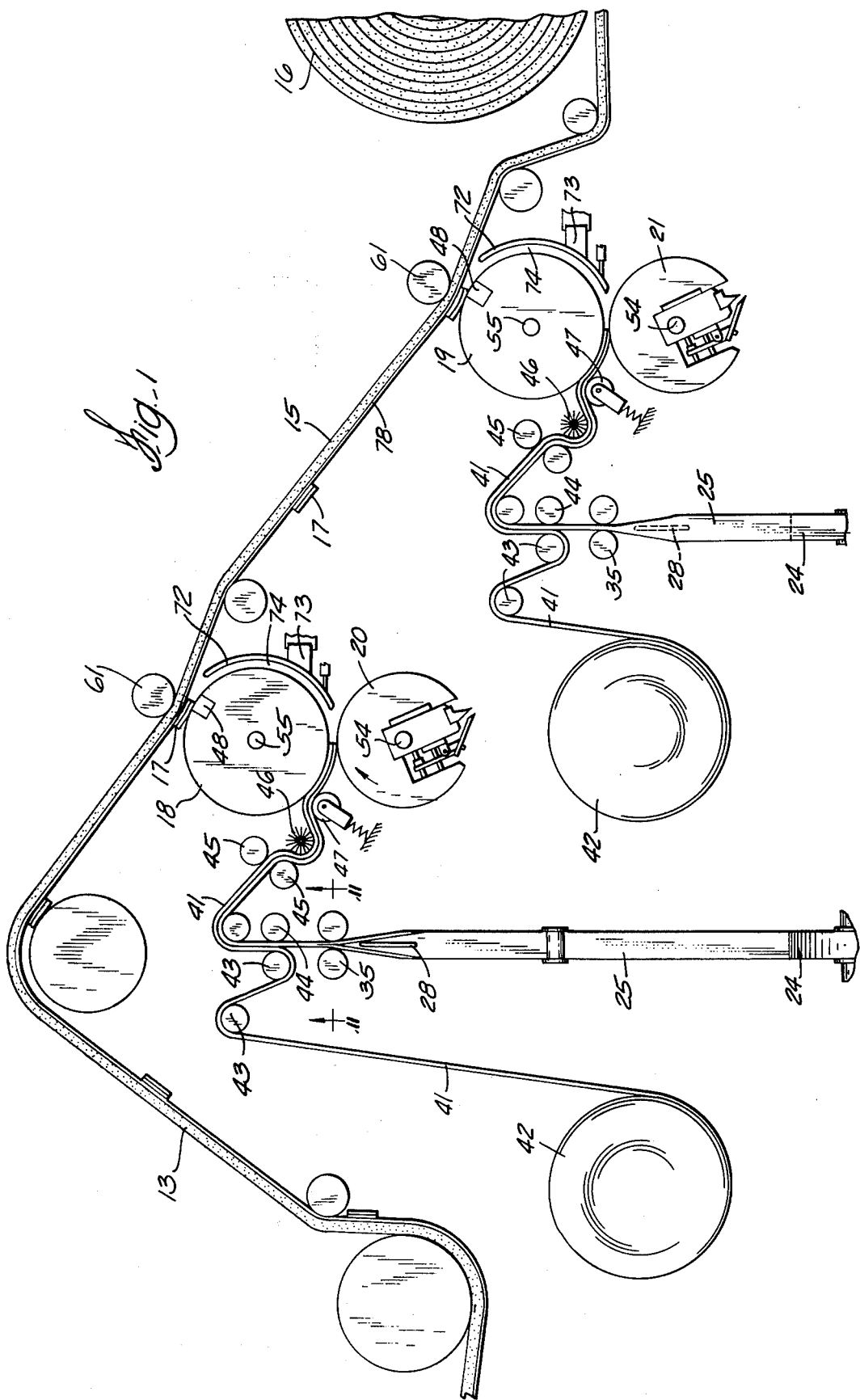
FIG. 1 is a diagrammatic side view of apparatus embodying the invention.
Figure 9:
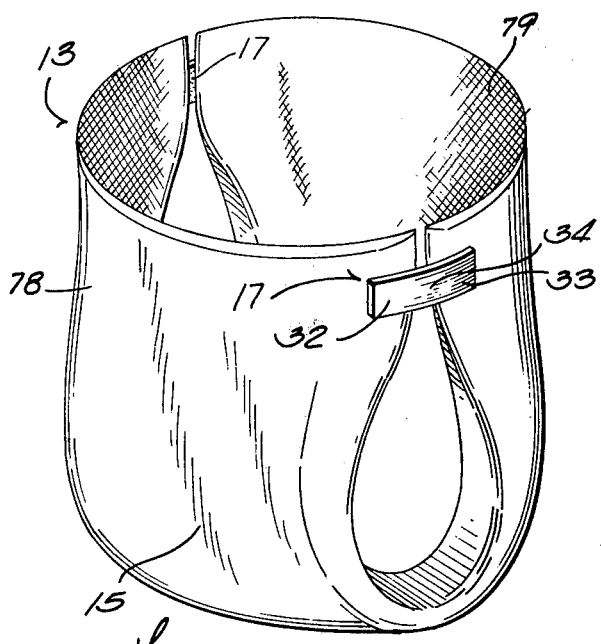
FIG. 9 is a perspective view illustrating the manner in which the tapes as applied to the pads are utilized to attach a diaper pad to a baby.

A continuous web or strip of composite, relatively thick workpiece pad material 15 may be unwound from a parent roll 16 generally on the path diagrammatically illustrated in FIG. 1. Ultimately, the web 15 will be severed into discrete workpiece pad segments 13 used as diapers or the like. In the case of a diaper 13, it is typically formed about a baby in the manner illustrated in FIG. 9. Diaper 13 typically comprises an outer plastic film backing ply 78, a pad filler (not shown) and an inner non-woven fabric ply 79, as shown in FIG. 9.

Prefolded attaching adhesive tape tab segments 17 are applied to opposite side margins of the pad web 15, as it travels on its path shown in FIG. 1, by a pair of vacuum drums or rotors 18, 19, one for each side margin of web 15. Drums 18, 19 function to transfer the folded tape segments 17 from the vicinity of rotating severing tools 20, 21 to the undersurface of the web 15.

FIGS. 1 and 7 illustrate the unwinding from parent rolls 24 of two relatively wide strips 25 of adhesive tape, each having a non-adhesive side 26 and an adhesive side 27. Each strip 25 is advanced to its folding blade or plow 28 which has an inclined edge 29 about which the strip 25 is folded, as illustrated in FIG. 7, to form a U-shaped strip having substantially flat wings 32, 33 connected on a hinge line 34. The non-adhesive side 26 of the tape is inside of the fold and the adhesive side of the strip 25 is on the outside of the fold.

Figure 11:
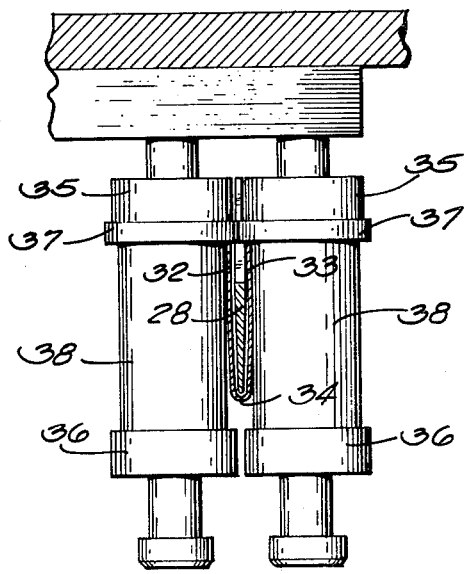
FIG. 11 is a cross section taken along the line 11—11 of FIG. 1.

To effectuate the folding aforesaid, the tape strip 25 is passed between forming roller 35 which, as best shown in FIGS. 7 and 11, have enlarged end collars 36, 37 which space the roll surfaces 38 apart sufficiently to receive the blade 28 therebetween and still leave room for the tape wings 32, 33 to fold about the blade 28 and to be guided thereabout by the rolls 38. Rolls 38 are desirably provided with a Teflon or like coating which is substantially non-adherent to the outwardly facing adhesive sides of the wings 32, 33.

Figure 12:
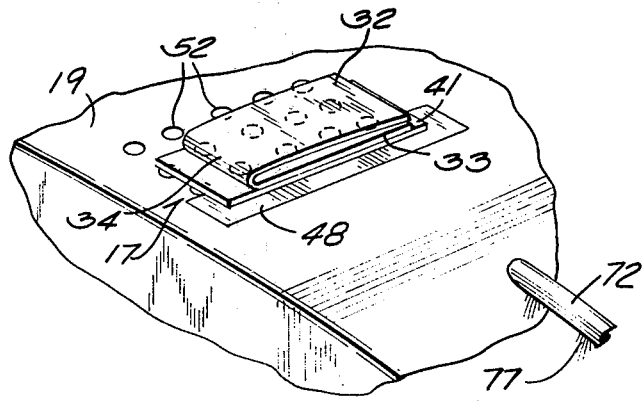
FIG. 12 is a fragmentary perspective view showing a folded tape segment adhered by vacuum to the vacuum drum.

As best shown in FIG. 1, a release tape liner strip 41 is applied to the exposed adhesive surface of one of the wings 32, 33 after tape 25 has been folded and before the composite strip has reached its vacuum drum 18, 19. The release liner strip 41 is so positioned as to be next adjacent the surface of its drum 18, 19 when applied thereto, as is also shown in FIG. 12.

Each liner 41 is drawn off its parent roll 42 and is guided by guiding rolls 43 and against a pressure roll 44 for firm adherence to the adhesive tape.

Paired drive rolls 45 are actuated to feed the respective composite tape strips around respective brush rollers 46 to a spring-biased idler roller 47 which presses its composite tape strip up against the surface of its drum 18, 19, as illustrated in FIG. 3. Drums 18, 19 each contain an anvil 48 which cooperates with a knife 51 on the rotating severing tool 20 for the purpose of severing the composite tape strips into discrete tape segments 17. The drums 18, 19 are provided in their surfaces adjacent anvil 48 with a vacuum pad comprising a pattern of vacuum holes 52 (FIG. 12) connected by vacuum ducts 53 to a source of vacuum, not illustrated, but which is conventional.

Figure 13:
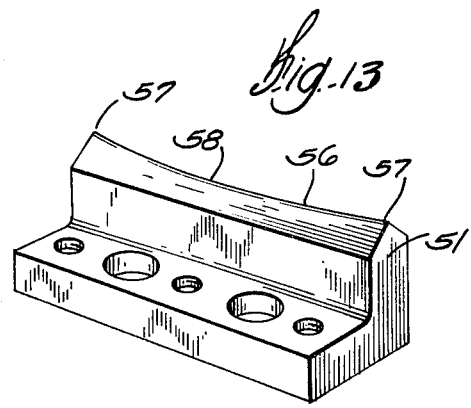
FIG. 13 is a perspective view of the knife, per se.

The rotating knife drums 20, 21 are mounted on axles 54 which are parallel to the axles 55 of the vacuum drums 18, 19. Knife blade 51 is provided with a curved knife edge 56, as illustrated in FIGS. 8 and 13, so that when it presses the composite tape strip 25, 41 against anvil 48, as illustrated in FIG. 5, the ends 57 of the knife will first penetrate the composite tape strip 25, 41 and the center portion or bow 58 of the knife will engage the tape strip 25, 41 later on, thus producing a shearing action of the knife 51 against the tape. This reduces shock and impact loads of the knife against the anvil.

Drums 18, 19 are rotated at a peripheral speed which matches the lineal speed of the pad web 15. The feed rollers 45 for the composite tape strips 25, 41 are independently controlled so as to feed the prefolded tape strips 25, 41 at a much slower speed. For each complete rotation of drums 18, 19, the feed rollers 45 advance short length of tape strip equal to the width of a tape segment 17 for each pad 13. Severed tape segment 17 is advanced by its drum 18, 19 while the tape strip from which the segment 17 has been severed slides on the drum periphery. Accordingly, the continuously rotating drum 18, 19 and coacting knife roll 20 will sever tape segments 17 from the tape strip 25, 41 and will transfer the discrete severed segment 17 from the vicinity of the knife 51 to a location on the pad 15 opposite a pressure roller 61.

The internal construction of one of the vacuum drums 18 and knife roll 20 is illustrated in FIGS. 3, 4, 5 and 6. The knife 51 is mounted on an insert block 62 which is clamped by suitable apparatus in a cavity formed in the knife roll 20. As illustrated in FIG. 5, the knife 51 coacts with the anvil block 48 in its drum 18, 19 to sever through the composite tape strip 25, 41. Prior to the coaction of the knife 51 with the anvil 48, the feed rolls 45 have fed the strip 25, 41 far enough to advance the tape segment 17 beyond the point of coaction of the knife 51 and the anvil 48 and into a position over the vacuum nozzles 52. Accordingly, in the position of the parts shown in FIG. 5 where the tape segment 17 has just been severed from the tape strip 25, 41, the segment 17 is held onto the vacuum drum by suction.

Each knife roll 20 is also provided with a finger blade 64 which performs several functions with respect to the tape segment 17. Tape segment 17 comprises wings 32, 33 folded about hingeline 34. Wing 33 to which the liner strip 41 has been applied is held directly against the drum by vacuum, as shown in FIG. 12. The resilience of the tape at hinge 34 tends to cause the other wing 32 to spring away from the drum, once the knife 51 has withdrawn from contact therewith. One function of finger blade 64 is to hold exposed wing 32 against lined wing 33 and prevent its springing away. Finger blade 64 is pivotally mounted to block 62 on pintle 65 and is subject to the action of spring 66 to urge finger blade 64 (clockwise in the drawings) toward engagement with the tape segment 17. However, finger blade 64 is yieldable against the bias of spring 66 and hence may swing away from the drum 18, as illustrated in FIG. 5. The precise positioning of the blade 64 can be adjusted by the thumb screw 68 which acts upon the end of lever 71 which mounts the blade 64 on the pintle 65. The desired adjustment is fixed by thumb nut 67.

Accordingly, the finger blade 64 will hold the folded tape segment 17 against the vacuum drum beyond the point where the knife 51 withdraws from the vacuum drum 18 and the spring biased mounting of the finger blade 64 will enable it to maintain contact with the folded tape segment 17 for a short arc of movement of the vacuum drum and knife roll 20.

The finger blade 64 also holds the tape segment against the drum as the knife 51 withdraws therefrom. Inasmuch as the knife edge presses against the exposed adhesive face of the tape, and tends to stick thereto, its withdrawal from the drum in the course of concurrent rotation of drums 18, 19, 20 would otherwise tend to strip the tape segment off of the drum. The finger blade 64 holds the tape segment against the drum during the withdrawal motion of the knife and strips the tape from the knife edge.

Beyond the point where the finger blade 64 loses contact with the folded tape segment 17, as shown in FIG. 6, further means are provided to hold exposed wing 32 of the tape segment against springing away from lined wing 33. Even though the vacuum of drums 18, 19 hold the lined wing 33 in position, the springing away of exposed wing 32 could cause problems when the tape segment 17 is pressed against the undersurface of pad web 15.

The added means for keeping the wings 32, 33 together comprises a hollow guide tube 72 for each drum 18, 19. Each tube 72 is curved about its drum 18, 19 and is substantially centered on the folded tape segment 17. Each guide tube 72 is mounted on a bracket 73 which, in turn, is mounted on a stationary part of the machine. Tubes 72 are spaced slightly from the drum surface to define narrow channels 74 through which the tape segments 17 must pass en route to the point of application to the undersurface of the pad 15. Accordingly, the tape wing 32 can function as a physical barrier or rail along which the exposed wing 32 may slide and be prevented from springing away from or unfolding with respect to lined tape wing 33.

The action of the guide 72 is desirably enhanced by making it hollow and providing a series of air nozzles 75 along its surface which faces the drum 18. Compressed air is fed to the hollow guide 72 through air pipe 76 and the air blast or jets 77 impinge on the exposed wing 32 to maintain the tape segment 17 folded. An air blast is preferred over frictional contact between the wing 32 and the guide 72, thus to reduce friction and minimize the possibility that the tape will become dislocated in the course of its transfer around the surface of the drums 18, 19.

The vacuum drums 18, 19 intersect the pad web 15 opposite pressure rolls 61 and the exposed adhesive wing 32 is pressed against the undersurface of the pads 13 and adheres thereto. The lined wings 33, which were against the drums 18, 19 are now outermost, as indicated in FIG. 10. The pad web 15 is oriented such that its plastic film component 78 is exposed to the tape 17, as shown in FIGS. 1 and 10.

As illustrated in FIGS. 1 and 2, the vacuum drum 19 is utilized to apply a series of tape segments 17 along one margin of the pad web 15 and the vacuum drum 18 is utilized to apply a corresponding series of tape segments 17 along the other side margin of the pad 15. The tape segments at opposite margins of the web 15 are arranged in laterally spaced paired relation, as is illustrated in FIG. 10. The hinge lines 34 of the respective segments 17 face opposite one another and the respective wings 32, 33 are located as indicated in this figure. The release liners 41 are outermost. Accordingly, when the pads 13 are applied to a baby as shown in FIG. 9 and the release liners 41 stripped from the tape wings 33, wings 33 may be swung about hinge 34 and applied to an adjacent portion of the pad, thus to interconnect opposite portions of pad 13 to diaper the baby. Inasmuch as the tape segments 17 are attached to the plastic film back 78 of the pads 13, utilization of the tape strips 17 will adhere the adhesive faces of the attaching tapes to the plastic diaper back 78 for firm adhesion thereto, no part of the tape being adhered to a paper or nonwoven or other fragile portion of the pad.

We claim:

1. Apparatus for applying adhesive attaching tapes to workpiece pads and comprising means for advancing to a tape folder an elongated strip of adhesive tape having an adhesive face and a non-adhesive back, tape folder means for folding the elongated tape strip along a longitudinally extending hinge line to form substantially flat tape wings having their non-adhesive backs together and their adhesive faces facing away from each other, means for applying a liner to the adhesive face of one of the wings while leaving the adhesive face of the other wing exposed, a movable vacuum pad, means to apply the lined wing of said elongated folded tape strip to the vacuum pad so that the lined wing is against the pad and the adhesive face of the other wing of the folded strip faces away from the pad, a severing tool to sever discrete folded tape segments from the folded elongated strip while the strip is held by vacuum on the vacuum pad, means for moving said vacuum pad beyond the point of severance and for applying the exposed adhesive face of said other wing to a portion of a workpiece pad, with said lined wing exposed and free for removal of the liner strip therefrom and free for unfolding said one wing about said hinge line for subsequent application to another portion of the workpiece pad.

2. The apparatus of claim 1 in combination with means for advancing an elongated workpiece pad on a path adjacent said vacuum pad.

3. The apparatus of claim 1 in combination with means for overcoming the tendency of said wings to spring apart about said hinge line and hence maintain the tape segment folded during rotation of the vacuum pad and until the adhesive face of the said other wing engages the workpiece pad.

4. The apparatus of claim 1 in which said vacuum pad is part of a drum and said severing tool comprises a rotary knife which coacts with the drum to sever the tape strip therebetween 5. The apparatus of claim 1 in combination with guide means to hold the tape segment to the vacuum pad as the knife withdraws from engagement with the tape.

6. The apparatus of claim 5 in which said guide means comprises a spring-actuated blade mounted ahead of the knife and which engages said tape segment during knife withdrawal.

7. The apparatus of claim 3 in which the means for maintaining the tape folded comprises a guide bar curved about the path of rotation of the vacuum pad and spaced therefrom to define a confined path within which the folded tape segment travels in the course of transfer from the knife to the pad.

8. The apparatus of claim 3 in which the means to maintain the tape folded comprises means for jetting air against the folded tape while it rotates with the vacuum pad from the vicinity of the knife to the vicinity of the pad.

9. The apparatus of claim 1 in which the tape folder comprises a blade against which a medial portion of the non-adhesive back of the tape strip is engaged to form a crease and tape guides at the sides of said blade to force said tape strip about the edges of the blade to dispose the substantially flat wings in back-to-back relation.

10. The apparatus of claim 9 in which said guides comprise rollers with ribs forming grooves within which said wings are received.

11. The apparatus of claim 1 in which said severing tool comprises a knife having an edge curved to produce a shear cut on the tape.

* * * * *